United States Patent [19]
Cardini et al.

[11] 3,934,039
[45] Jan. 20, 1976

[54] PROCESS FOR THE PRODUCTION OF MICROORGANISM LYSATES

[75] Inventors: Giuliano Cardini; Aldo Zotti, both of Milan, Italy

[73] Assignee: Societa' Italiana Resine S.p.A., Milan, Italy

[22] Filed: Nov. 29, 1973

[21] Appl. No.: 420,346

[30] Foreign Application Priority Data
Nov. 30, 1972 Italy .................................. 32277/72

[52] U.S. Cl. .................. 426/7; 426/60; 426/656
[51] Int. Cl.² ........................................... A23J 1/18
[58] Field of Search ........ 426/60, 61, 62, 204, 364, 426/212, 356, 7; 195/2, 4, 104, 1, 96, 98

[56] References Cited
UNITED STATES PATENTS

| | | | |
|---|---|---|---|
| 2,928,740 | 3/1960 | Rosenthal et al. | 426/60 X |
| 3,615,685 | 10/1971 | Fantozzi et al. | 426/62 |
| 3,720,585 | 3/1973 | Tannenbaum et al. | 426/62 X |

*Primary Examiner*—Raymond N. Jones
*Assistant Examiner*—Esther L. Massung
*Attorney, Agent, or Firm*—Sughrue, Rothwell, Mion, Zinn & Macpeak

[57] ABSTRACT

Process for the production of microorganism lysates, comprising subjecting the said microorganisms suspended in water to thermal shock produced by a spray-drying treatment and then subjecting the product resulting from spray drying to autolysis.

5 Claims, No Drawings

PROCESS FOR THE PRODUCTION OF MICROORGANISM LYSATES

The present invention relates to the production of nitrogenous material from microorganisms, and more particularly to an improved process for obtaining lysates from the said microorganisms.

DESCRIPTION OF THE PRIOR ART

For a long time, the only unicellular organism used by man as food was represented by the yeasts, whose production on the industrial scale was almost exclusively due to the large quantities of yeast required for raising of bread.

The idea of the industrial-scale production of foods from microorganisms for human or animal use is fairly recent. The cell protoplasm of yeasts and of bacteria consists largely of proteins and to a smaller extent of carbohydrates, lipids, nucleic acids, vitamins, and intermediate metabolites.

The knowledge of the large quantity of nutrient principles contained in the cells of yeasts and bacteria and the need to find new sources of food for man drove investigators to examine the possibility of producing foods for human and animal use from yeasts and bacteria industrially and at low cost.

The industrial processes developed so far, both for yeasts and for bacteria, may be carried out either discontinuously or continuously and consist of two fundamental stages.

The first of these stages consist in inoculating a liquid growth medium with a microorganism, allowing the microorganism to grow until the growth reaches a steady state, and finally separating the microorganism cells from the culture medium.

The liquid growth medium consists of water containing an assimilable nitrogen source, an assimilable carbon source, and inorganic salts.

To improve the economy of this stage of the process, the efforts of the technicians were directed mainly towards the discovery of cheaper materials that could be used as assimilable carbon sources. Molasses sulphite liquor, wood hydrolysates, and vegetable waste have been used for this purpose. The most significant advance in this field during the last few years was the discovery that the microorganisms can ferment paraffins, and particularly the fraction containing from 10 to 30 carbon atoms per molecule.

The method for separating the microorganisms from the culture medium, which is the final operation in this stage of the process, varies with the composition of the medium. When hydrocarbons are used as carbon sources, the cells are separated from the growth medium by flocculation, sedimentation, or centrifugation and resuspended in water, possibly containing a small quantity of surfactant. After vigorous agitation, the cells are again separated from the liquid phase. This operation is repeated several times until the cells are practically free from hydrocarbons.

The second stage in the processes for the production of foodstuffs from microorganisms consists essentially of treatments that allow the separation of the protoplasm from the materials forming the cell wall.

This stage of the process was made necessary by the fact that the microorganism cells, when used unaltered, do not constitute a satisfactory food for animal or human use, despite their high protein content. This is due partly to the low digestibility of the cell wall and partly to the impermeability of the membrane that encloses the protoplasm.

The two teguments together thus effectively oppose the escape of the protoplasm and hence allow difficult and only partial assimilation of the nutrient principles contained in the cell by the animal or human organism.

An advantage of lysis is that once the protoplasm has been extracted from the interior of the cell, the lipids present in it can be easily separated from the other constituent substances.

This is very important, both because the lipids are less valuable, give the microorganism an unpleasant taste and odor and because after these have been separated, it is possible to recover from them large quantities of sterols, particularly ergosterol, which is the starting material for the preparation of vitamin D2.

The cell also contains other unwanted substances such as the nucleic acids, which are dangerous to the consumer's health when present in high concentrations, and the pigments (chlorophylls, xanthophyll, etc.), which reduce the value of the product by giving it an excessively intense color.

Both of these groups of products can be easily eliminated from the cell by previous lytic treatment and can be collected separately and purified for use as additives in the food industry.

Among the methods commonly used for the extraction of the protoplasm from the interior of the microorganism cells, hydrolysis, plasmolysis, and autolysis are of interest from the industrial point of view.

Hydrolysis is carried out by suspending the microorganism cells in an acidic or alkaline aqueous solution. The cell membrane is attacked by the acid or by the base, and this leads to its rupture and hence to the escape of the protoplasm through the holes in the cell wall. The process is fairly fast and complete, but considerable loss of valuable material occurs as a result of the degradation of the constituents of the protoplasm by the acid or the alkali.

Plasmolysis is carried out by suspending the microorganism cells in an aqueous solution containing high concentrations of inorganic salts or organic substances such as sugars. This leads to modification of the osmotic characteristics of the cell membrane and hence to the escape of the protoplasm from the interior of the cell. No degradation of the constituents of the protoplasm occurs in such a process, but useful material is still lost, since the escape of the protoplasm is not complete. Moreover, the separation of the useful substances from the aqueous phase is difficult because of the presence of inorganic salts or of the organic compounds in high concentrations.

Autolysis, which is generally preferred to hydrolysis and plasmolysis, is carried out by suspending the microorganism cells in water, adjusting the suspension to a certain pH, and heating. This causes rupture of the cell membrane by the action of enzymes contained in the cell itself, and hence the escape of the protoplasm.

The pH and temperature conditions used depend on the nature of the enzymes contained in the cell. The operating temperatures used are generally in the range from 45° to 55°C.

However, autolysis also is not an efficient process under these conditions, since the rupture of the cell membrane does not occur for all the cells present, and in any case the lysis is not sufficiently extensive to allow the complete escape of the intracellular substances.

SUMMARY

One object of the invention is to provide a simple and efficient process for the production of microorganism lysates, which allows one to obtain a complete autolysis of the microorganism cells. Another object is to provide a process for the production of microorganism lysates which is carried out under mild conditions and without degradation of useful materials.

The present invention is based essentially on the discovery that practically complete autolysis can be achieved under mild conditions and without degradation of the useful materials if the microorganisms suspended in water are previously subjected to a thermal shock produced by a spray-drying treatment.

The process of the present invention therefore consists essentially in suspending in water microorganism cells obtained by appropriate fermentation procedure, then subjecting the said suspension to thermal shock by spray drying and finally subjecting the resulting product to autolysis.

When carrying out the process of the invention any microorganism cells and preferably yeasts may be used.

During the spray-drying treatment, most of the water is removed from the suspension, and it is thought that changes are simultaneously brought about in the cells that make them more susceptible to autolysis.

Whatever the explanation, the fact is that spray drying has the effect of increasing the yield of the autolysis, even when the said autolysis is carried out under extremely mild conditions.

It is found that the best results are obtained by the use of suspensions containing from about 5 to 15% by weight of microorganism cells, the said suspensions being fed into spraying, pulverizing, or atomizing equipment or prilling towers into which air or an inert gas such as nitrogen is fed as an evaporating medium.

The dried product is thus collected at the base of the drier in the form of granules or powder.

It is essential for the purposes of the present invention to regulate the drying conditions in such a way that the water content of the treated product is less than about 10% by weight.

To this end, the air or the inert gas used as the evaporating medium is preheated to temperatures of from about 150° to 400°C before introduction into the drier. It is found that the best conditions are obtained when the gas introduced is preheated to about 200° to 250°C and the contact times between the said gas and the product subjected to drying are from about 1 to 40 seconds and preferably from about 5 to 20 seconds.

In this way, a product at a temperature of from about 30° to 90°C having a water content of from about 5 to 8% by weight, which is particularly suitable for the autolysis process, is collected at the base of the drier.

The microorganism cells treated in this way are then suspended in water normally in quantities of one part by weight of the said cells per two parts by weight of water.

The suspension is heated with or without agitation at a temperature of from about 30° to 50°C and for a time of from about 10 to 48 hours.

The best results are obtained with a temperature of about 45°C and with a time of from about 24 to 40 hours.

During this phase, through the action of the autolytic enzymes, a profound lytic alteration of the cell membrane and probably of the cell wall of the microorganisms occurs, with consequent escape of the protoplasm.

During the autolysis treatment, organic or inorganic substances may be present.

Examples of such substances, which are added in quantities of from about 1 to 100 milligrams per kg of dry cells, are salts of magnesium, calcium, or zinc, such as sulphates or halides, particularly chlorides, or ethylenediaminetetraacetic acid, particularly the sodium salt of this acid.

At the end of the autolysis, the aqueous suspension is suitably diluted and the cell content (particularly protein) is separated by centrifugation from the insoluble residues of the cell walls.

The solid residue is then extracted with a dilute solution of sodium hydroxide to bring about the solubilization of any protein fraction that may have precipitated.

The combined protein extracts are intended for human or animal food as such or after further purification.

For example, the proteins separated from the cell walls as described above can be further purified through separation by precipitation with acids or with salts, electrophoresis, chromatography, etc.

The process of the present invention is applicable to yeasts or other microorganisms obtained in various ways, for example in the fermentation of sulphite residues, molasses, paraffins, etc.

In the following experimental examples, autolysis is carried out on the yeasts obtained by fermentation of linear paraffins by a process that comprises the stages of fermentation, separation, and washing.

In the first stage, the yeasts are brought into contact with the linear paraffins in a strongly aerated liquid medium. The result is the growth of the cells at the expense of the hydrocarbon.

At the end of the growth, the cells are separated from the culture broth by flocculation, sedimentation, or centrifugation, and the said cells are then resuspended in water to which a small quantity of surfactant is also added.

After vigorous agitation, the cells are again separated from the liquid phase.

Water is then again added and the cells are separated.

This operation is repeated several times until cells that are practically free from hydrocarbons are obtained.

After the final wash, the content of the cells in the aqueous suspension is adjusted to a value of from about 5 to 15% by weight and the suspension is subjected to spray drying.

The invention is further illustrated by the following non-limiting examples.

Example 1

A fermentation broth containing water, nitrogen sources, inorganic salts, and a mixture of linear paraffins with an average molecular weight of about 200 is inoculated with a strain of *Candida lipolytica* and then kept agitated by introduction of air, at a temperature of 30°C, for 64 hours.

At the end of this time, in which the growth occurs, the cells are separated from the exhausted broth by centrifugation, and after repeated washing with water, are adjusted to a concentration of 10% by weight.

The yeast suspension obtained in this way is subjected to thermal shock by spray drying in accordance with the process of the present invention. More particularly, the said yeast suspension is fed under pressure to the top of a spray drier in the form of a vertical cylinder.

Air preheated to a temperature of 240°C is introduced at the base of the drier.

The drier is also provided with lateral holes towards the top end for the removal of the air, the exit temperature of which is 70°C.

With a contact time of about 15 seconds, a product having the following composition, expressed in % by weight, is collected in the basin at the base of the drier:

| | |
|---|---|
| water | 6% |
| lipids | 4% |
| ash | 7% |
| fibre | 1% |
| protein | 50% |
| non-nitrogenous products | 32% |

100 grams of yeast subjected to spray drying are suspended and homogenized in 200 ml of deionized water and the suspension is kept at 40°C for 40 hours.

At the end of the incubation, the product is centrifuged at about 2000 x g and the contents of nitrogen and of dry solids are determined in the supernatant.

Analysis shows that 75% of the nitrogen and 60% of the original yeast are recovered in the soluble form.

Example 2

100 grams of yeast obtained by fermentation as described in Example 1 are subjected to autolysis under the same conditions as in Example 1 but without the previous spray-drying treatment.

At the end of the incubation according to example 1 the product is centrifuged at about 2000 x g and the contents of nitrogen and of dry solids are determined in the supernatant.

Analysis shows that 50% of the nitrogen and 45% of the original yeast are recovered in the soluble form.

What we claim is:

1. A process for the production of microorganism lysates, which comprises preparing an aqueous suspension containing 5 to 15% by weight of the microorganisms cells; thermal shocking the microorganisms by spray-drying by introducing the aqueous suspension of the microorganisms into spraying, pulverising, or atomizing equipment or prilling towers, feeding air or an inert gas as the evaporating medium into said equipment, said gas being preheated to a temperature of from about 150° to 400°C, for a contact time of from about 1 to 40 seconds to reduce the water content of the suspension of microorganisms to below about 10% by weight; suspending the product resulting from the spray-drying treatment in water and subjecting the microorganisms suspended in water to autolysis by heating said suspension to a temperature of from about 30° to 50°C for a time of from about 10 to 48 hours.

2. The process of claim 1 wherein the inert gas is nitrogen.

3. The process of claim 1 wherein the contact time is about 5 to 20 seconds and the temperature of preheating is from about 200° to 250°C.

4. The process of claim 1 wherein the water content of the spray-dryed product is about 5 to 8% by weight.

5. The process of claim 1 wherein autolysis is carried out at a temperature of about 45°C for a time of from about 24 to 40 hours.

* * * * *